United States Patent
Ge et al.

(10) Patent No.: US 11,197,850 B2
(45) Date of Patent: Dec. 14, 2021

(54) POWDER INJECTION OF THE DONEPEZIL SEMI PALMOXIRIC ACID SALT, COMPOSITION CONTAINING SAME AND PREPARATION METHOD THEREFOR

(71) Applicants: Shanghai Synergy Pharmaceutical Sciences Co., Ltd, Shanghai (CN); Zhejiang Huahai Pharmaceutical Co., Ltd, Zhejiang (CN)

(72) Inventors: Jian Ge, Shanghai (CN); Yunfei Li, Shanghai (CN); Lihong Lin, Zhejiang (CN); Dengxue Sun, Zhejiang (CN); Jiamiao Wang, Shanghai (CN); Yijin Wang, Shanghai (CN); Zhiyun Wang, Zhejiang (CN)

(73) Assignees: Shanghai Synergy Pharmaceutical Sciences Co., Ltd., Shanghai (CN); Zhejiang Huahai Pharmaceutical Co., Ltd., Zhejiang (CN)

( * ) Notice: Subject to any disclaimer, the term of this patent is extended or adjusted under 35 U.S.C. 154(b) by 3 days.

(21) Appl. No.: 16/465,116

(22) PCT Filed: Feb. 13, 2018

(86) PCT No.: PCT/CN2018/076599
§ 371 (c)(1),
(2) Date: May 29, 2019

(87) PCT Pub. No.: WO2018/153315
PCT Pub. Date: Aug. 30, 2018

(65) Prior Publication Data
US 2020/0108055 A1  Apr. 9, 2020

(30) Foreign Application Priority Data
Feb. 23, 2017 (CN) .......................... 201710099184.5

(51) Int. Cl.
| | | |
|---|---|---|
| A61K 31/445 | (2006.01) |
| A61K 9/00 | (2006.01) |
| A61K 9/16 | (2006.01) |
| A61K 47/02 | (2006.01) |
| A61K 47/26 | (2006.01) |
| A61K 47/34 | (2017.01) |
| A61K 47/38 | (2006.01) |

(52) U.S. Cl.
CPC .......... *A61K 31/445* (2013.01); *A61K 9/0019* (2013.01); *A61K 9/16* (2013.01); *A61K 9/1688* (2013.01); *A61K 47/02* (2013.01); *A61K 47/26* (2013.01); *A61K 47/34* (2013.01); *A61K 47/38* (2013.01)

(58) Field of Classification Search
CPC .. A61K 31/445; A61K 9/0019; A61K 9/1688; A61K 47/02; A61K 47/34
See application file for complete search history.

(56) References Cited

U.S. PATENT DOCUMENTS

| | | | | |
|---|---|---|---|---|
| 4,681,927 A | * | 7/1987 | Umemura ................ | C08G 2/18 528/232 |
| 2004/0146562 A1 | * | 7/2004 | Shah ................... | A61K 31/496 424/486 |
| 2014/0243278 A1 | | 8/2014 | Nadkarni et al. | |
| 2014/0315952 A1 | * | 10/2014 | Gu ........................ | A61K 31/27 514/319 |
| 2015/0216849 A1 | * | 8/2015 | Dedhiya ................ | A61P 43/00 514/317 |

FOREIGN PATENT DOCUMENTS

| | | |
|---|---|---|
| CN | 101039910 A | 9/2007 |
| CN | 104039765 A | 9/2014 |
| CN | 105338966 A | 2/2016 |

OTHER PUBLICATIONS

Mesh to Micron Conversion Chart, retrieved online from Google search Oct. 21, 2020.*

* cited by examiner

*Primary Examiner* — Mina Haghighatian
(74) *Attorney, Agent, or Firm* — Umberg Zipser LLP; Jason Tejani

(57) ABSTRACT

A powder injection of a donepezil semi palmoxiric acid salt, a composition containing the same and a preparation method therefor. The powder injection contains donepezil semi palmoxiric acid salt crystals, and the average grain size of the crystals ranges from 0.5 μm to 100 μm.

2 Claims, No Drawings

POWDER INJECTION OF THE DONEPEZIL SEMI PALMOXIRIC ACID SALT, COMPOSITION CONTAINING SAME AND PREPARATION METHOD THEREFOR

This application claims the priority of Chinese Patent Application No. 201710099184.5, filed before the CNIPA on Feb. 23, 2017, titled "powder injection of donepezil semi pamoate for injection and preparation method thereof", which is incorporated herein by reference in its entirety.

FIELD OF THE INVENTION

The present disclosure pertains to the technical field of medicament preparation, in particular to a method for preparing a powder injection of donepezil semi pamoate.

BACKGROUND OF THE INVENTION

Alzheimer disease (AD) has a complex pathogenesis and is a result of multifactorial interactions. The commonly accepted hypotheses at present include: cholinergic damage hypothesis, excitatory amino acid toxicity hypothesis, amyloid β-protein (Aβ) cascade hypothesis, Tau protein hyperphosphorylation hypothesis and oxidative stress hypothesis. The US Food and Drug Administration (FDA) currently only approves five medicaments for the treatment of AD, four of which are acetylcholinesterase inhibitors (AChEIs), namely, tacrine (1993), donepezil (1996), rivastigmine (2000), and galantamine (2001), and another is an antagonist of N-methyl-D-aspartic acid (NMDA) receptor, namely memantine (2003). Among them, tacrine has been basically abandoned due to the requirement of 4 times administeration per day and the potential severe hepatotoxicity. The other four medicaments are currently the first-line drugs for the treatment of AD, which can moderately improve the cognitive ability, the ability of daily life, mental behavior and overall function of AD patients, and have good safety and tolerance. Donepezil, rivastigmine and galantamine have equal efficacy, while donepezil is superior in safety, tolerance and patient compliance. In China, the commonly used medicaments for AD treatment include: huperzine A, donepezil, piracetam, oxiracetam, pyritinol, nimodipine, citicoline, ginkgo extract, dihydroergotoxine, memantine, acetylglutamine, and idebenone, etc.

Donepezil is an effective medicament for AD treatment in both domestic and foreign markets. It has a high selectivity and a reversible treatment of AD. However, conventional preparations require daily administration. The senile dementia patients have poor compliance, and they cannot take medicine at the specified dose on time, thus seriously affecting treatment effects. In order to solve the problems caused by the conventional preparations of donepezil, domestic and foreign scholars have made various attempts on long-acting donepezil preparations. At present, many technologies for long-acting donepezil preparations have been disclosed, as described in patents such as US2011/0218216, WO2010/039381, CN101167697, CN1602867, and CN103316974. However, these long-acting preparations also have problems in the high manufacturing cost and difficulty in production on a commercial scale. There is still a need to improve the preparation process of donepezil to fully exert the efficacy of donepezil and maximize its medical benefits.

SUMMARY OF THE INVENTION

An object of the present disclosure is to provide a powder injection of donepezil semi pamoate, a composition containing the same and a preparation method thereof. The object of the present disclosure is realized by the following technical solutions.

Firstly, the present disclosure provides a powder injection of donepezil semi pamoate comprising donepezil semi pamoate crystals having an average particle size ($D_{50}$) 0.5-200 μm, or not less than 180 μm, or not less than 160 μm, or not less than 140 μm, or not less than 120 μm, or not less than 100 μm, or not less than 80 pin, or not less than 60 μm, or not less than 30 μm, or not less than 10 μm, preferably 0.5-52 μm, more preferably 2-32 μm, and still more preferably 4-15 μm.

In some embodiments of the present disclosure, the donepezil semi pamoate crystals have an angle of repose 25-46 degrees, preferably 32-43 degrees.

The present disclosure provides a method for preparing a powder injection of donepezil semi pamoate, comprising: crystallizing donepezil semi pamoate, subjecting to a dry pulverization, optionally filling into a sterilization container, and then subjecting to a sterilization process.

In some specific embodiments of the present disclosure, the method for preparing the powder injection of donepezil semi pamoate may comprise the following steps:
  step 1: dissolving donepezil hydrochloride in purified water, stirring, and filtering to obtain a filtrate;
  step 2: dissolving disodium pamoate in purified water, stirring, and filtering to obtain a filtrate; and
  step 3: adding donepezil semi pamoate seed crystals to the filtrate obtained in step 1 to obtain a solution; then dropwise adding the filtrate obtained in step 2 into the above solution, stirring for 1-2 hours, filtering to obtain a filter cake; washing the filter cake with purified water, drying, and performing a dry pulverization and a sterilization process.

The dry pulverization is selected from the group consisting of a sieve pulverization, a ball milling pulverization and/or a jet pulverization.

The sterilization process in the above preparation method is a γ-ray irradiation sterilization, an electron beam irradiation sterilization or a microwave irradiation sterilization, preferably an electron beam irradiation sterilization, and an irradiation dose of the electron beam irradiation sterilization is 25 kGy to 60 kGy. The sterilization container can be made of borosilicate glass with pyrogens removed.

In some specific embodiments of the present disclosure, in particular, the dry pulverization may be performed by using a sieve pulverizer equipped with a 10-20 mesh sieve.

The present disclosure also provides a composition comprising donepezil semi pamoate, which comprises the aforementioned powder injection of donepezil semi pamoate or the powder injection of donepezil semi pamoate obtained by the aforementioned method.

In some embodiments of the present disclosure, the powder injection of donepezil semi pamoate is present in 13%-24% by mass, based on total mass of the composition.

In some embodiments of the present disclosure, the composition further comprises a diluent; preferably, based on total mass of the diluent, the diluent comprises 0.03%-3% of a suspending agent, 3%-6% of a tension agent, and 0.03%-2% of a wetting agent by mass.

In some embodiments of the present disclosure, the suspending agent is one or more selected from the group consisting of methylcellulose, sodium carboxymethylcellulose, hydroxypropylmethylcellulose, polyvinylpyrrolidone, alginate, chitosan, glucan, gelatin, polyethylene glycol, polyoxyethylene ether, and polyoxypropylene ether, preferably sodium carboxymethylcellulose (CMC-Na). The tension agent is one or more selected from the group consisting of sodium chloride, dextrose, mannitol, sorbitol, lactose, and sodium sulfate, preferably mannitol or sodium chloride. The wetting agent is one or more selected from the group consisting of polysorbate 80, polysorbate 20, poloxamer, lecithin, polyoxyethylene ether, polyoxypropylene ether, and sodium deoxycholate, preferably poloxamer 188 or Tween 80.

In some embodiments of the present disclosure, the suspending agent may also range from 0.5% to 1.5%, preferably from 0.75% to 1.5%, the wetting agent may also range from 0.05% to 0.5%, preferably from 0.05% to 0.2%, and the tension agent may also range from 4.5% to 5% or from 4.5% to 6%.

The present disclosure still further provides a method for preparing an injection of donepezil semi pamoate, which is characterized by following steps:

(1) obtaining the aforementioned powder injection of donepezil semi pamoate, or the powder injection of donepezil semi pamoate obtained by the method of any one of the preceding embodiments; and (2) mixing the powder injection of step (1) with a diluent to obtain an injection of donepezil semi pamoate, wherein based on total mass of the diluent, the diluent comprises 0.03%-3% of a suspending agent, 3%-6% of a tension agent, 0.03%-2% of a wetting agent by mass and water for injection.

In some embodiments of the present disclosure, the suspending agent may also range from 0.5% to 1.5%, preferably from 0.75% to 1.5%; the wetting agent may also range from 0.05% to 0.5%, preferably from 0.05% to 0.2%; and the tension agent may also range from 4.5% to 6%. The suspending agent is preferably CMC-Na; the tension agent is preferably mannitol or sodium chloride; and the wetting agent is preferably poloxamer 188 or Tween 80.

The powder injection of donepezil semi pamoate provided in the present disclosure has a reduced stimulation of the medicament by controlling the particle size of the medicament. Further, the powder injection of donepezil semi pamoate provided in the present disclosure has good fluidity and is easier for dispensing. Certainly, it is not necessary to achieve all of the advantages described above when implementing any one of the product of the present disclosure.

DETAILED DESCRIPTION OF THE INVENTION

In order to make the objects, technical solutions, and advantages of the present disclosure more clear, the present disclosure will be further described in detail below with reference to the examples of the disclosure. It is apparent that the described examples are only a part but not all of the examples of the present disclosure. All other examples obtained by those skilled in the art based on the examples of the present disclosure without creative efforts are within the protection scope of the present disclosure.

Example 1: Preparation of Powder Injection of Donepezil Semi Pamoate

1. Preparation of Medicament Powders Having Different Particle Size (1) Preparation of Powder 1 #

Step 1: 6.6 g of donepezil hydrochloride was dissolved in 250 ml of purified water and stirred. 0.34 g of activated carbon was added, and stirred at 40-60° C. for 1-2 hours. The reaction solution was cooled to room temperature and filtered. The filtrate was retained for use.

Step 2: 3.7 g of disodium pamoate was dissolved in 250 ml of purified water and stirred. 0.18 g of activated carbon was added, and stirred at 40-60° C. for 1-2 hours. The reaction solution was cooled to room temperature and filtered. The filtrate was retained for use.

Step 3: 0.2 g of donepezil semi pamoate seed crystals (the preparation method refers to example 4 of patent WO2013078608) were added into the filtrate obtained in step 1 to obtain a solution. Then the filtrate obtained in step 2 was slowly and dropwise added into the above solution at room temperature over 1 hour, slowly stirred for 5-10 hours with an anchor stir bar and filtered. The resulting filter cake was washed with purified water and dried to finally obtain 9.6 g of solid particles of donepezil semi pamoate. The obtained particles have an average particle size $D_{50}$ of 90±17 μM as measured by a laser ganulometer.

(2) Preparation of Powder 2 #

Step 1 and step 2 are the same as those of powder 1 #. Step 3: 0.2 g of donepezil semi pamoate seed crystals (the preparation method is the same as above) were added into the filtrate obtained in step 1 to obtain a solution. Then the filtrate obtained in step 2 was slowly and dropwise added into the above solution at 4-10° C. over 1 hour, stirred for 1-2 hours at room temperature and filtered. The resulting filter cake was washed with purified water, dried, and then put into a pulverizer equipped with a 10 mesh sieve one by one to finally obtain 8.1 g of solid particles of donepezil semi pamoate. The obtained particles have an average particle size $D_{50}$ of 42±10 μM as measured by a laser granulometer.

(3) Preparation of Powder 3 #

Step 1 and step 2 are the same as those of powder 1 #. Step 3: 0.2 g of donepezil semi pamoate seed crystals (the preparation method refers to patent WO2013078608) were added into the filtrate obtained in step 1 to obtain a solution. Then the obtained solution was heated to 50-60° C. The filtrate obtained in step 2 was slowly and dropwise added into the above solution. After completion of the addition, the reaction solution was cooled to room temperature, stirred for 1-2 hours, and filtered. The resulting filter cake was washed with purified water, dried, and then put into a sieve pulverizer equipped with a 20 mesh sieve one by one to finally obtain 8.9 g of solid particles of donepezil semi pamoate (with a yield of 91%). The obtained particles have an average particle size $D_{50}$ of 13±2 μM as measured by a laser granulometer.

(4) Preparation of Powder 4 #

The powder 3 # prepared above was further subjected to ultrafine pulverization by a jet mill.

Pulverization conditions: the pressure when the powder was injected into the ultrafine pulverizer was 0.8-1.15 MP; the working pressure of the ultrafine pulverizer was 0.7-1.2 MP; and the pulverizing time was 30 minutes.

The obtained particles have an average particle size $D_{50}$ of 3±1 μM as measured by a laser granulometer.

(5) Preparation of Powder 5 #

The powder 4 # prepared above was further subjected to ultrafine pulverization by a jet mill.

Pulverization conditions: the pressure when the powder was injected into the ultrafine pulverizer was 0.8-1.15 MP: the working pressure of the ultrafine pulverizer was 0.7-1.2 MP; and the pulverizing time was 90 minutes.

The obtained particles have an average particle size $D_{50}$ of 0.9±0.4 μM as measured by a laser granulometer.

2. Study on Sterilization Conditions for Powder Injection of Donepezil Semi Pamoate (1) Assessment of Stability of Medicament Powders Under Dry Heat Sterilization Conditions The powder 3 # prepared in Example 1 was placed at 160° C. for 2 hours, and the changes in appearance and weight loss thereof were recorded. The results showed that after 2 hours, the powder sample gradually changed from light yellow to bright brown, and finally coagulated and melted. In addition, a weight loss of about 5.14% was observed. These results indicate that donepezil semi pamoate powder cannot tolerate the dry heat sterilization condition of 160° C.

(2) Assessment of Stability of Medicament Powders Under Electron Beam (E-Beam) Irradiation Sterilization Conditions The powder 3 # prepared in Example 1 was dispensed into a 6 ml borosilicate glass container with pyrogens removed, and then irradiated with different surface irradiation doses of 20 kGy, 30 kGy, 40 kGy, 50 kGy or 60 kGy respectively. Then an acceleration stability study was performed by placing the powder bottles at 40° C. under a relative humidity of 75% for storage. The tests were performed by sampling at time points of 1 month, 2 months, 3 months, and 6 months after sterilization, respectively.

The test results show that the medicament powders can be stored for a further extended period under the acceleration stability condition after sterilization by E-beam irradiation with the sterilization dose of 60 kGy, and remain stable, with total impurities of no more than 0.3% and unknown impurities of no more than 0.1%. There were no significant changes in key physicochemical properties such as appearance, identification, impurities, water content and particle size distribution during the acceleration test. Therefore, it can be confirmed that E-beam sterilization with a sterilization dose of 60 kGy or less does not adversely affect the basic properties of the medicament.

For the above medicament powders, the best sterilization method is irradiation sterilization, including γ-ray electron beam irradiation and microwave irradiation.

Example 2: Appearance and Fluidity Test of Powder Injection of Donepezil Semi Pamoate The angle of repose is a common index for evaluating the fluidity of dry powder. When measuring the angle of repose, the funnel is fixed at a suitable height H. The dry powder prepared in Example 1 was placed in a funnel and naturally leaked to form a pile until tip of the cone almost contacts the outlet of the funnel. Then, the radius r of the bottom surface of the cone was measured, and the angle of repose is arctg (H/r).

The appearance of each of the medicament powders prepared in Example 1 was observed and the angle of repose was measured, as shown in Table 1:

TABLE 1

| Samples | Appearance observed | Angle of repose (°) |
| --- | --- | --- |
| Powder 1# | Homogeneous solid particles | 28 ± 4 |
| Powder 2# | Homogeneous solid particles | 35 ± 3 |
| Powder 3# | Homogeneous solid particles | 42 ± 1 |
| Powder 4# | Homogeneous solid particles | 38 ± 3 |
| Powder 5# | Obvious static electricity, and serious agglomeration | 50 ± 4 |

The general rule deems that powder is very free flowing when its angle of repose is ≤9°; powder is free flowing when its angle of repose is 20-29°; powder is general flowing when its angle of repose is 30-39°; and powder is slow flowing when its angle of repose is ≥40°.

It can be seen from the above table that among the five powders with different particle sizes, powder 5 # has a poor fluidity, obvious static electricity, and serious agglomeration, while powders 1 #, 2 #, 4 # and 3 # all have certain fluidity.

Example 3: Study of Formulation for Powder Injection of Donepezil Semi Pamoate 1. Suspension Property Study.

The powder 3 # prepared in Example 1 was placed in different diluents to formulate a suspension having a concentration of 230 mg/mL to obtain different formulations. The diluents contained 0.75%-1.5% of sodium carboxymethyl cellulose (CMC-Na), and 0.05%-0.20% of poloxamer 188 or Tween 80. The suspension was then vibrated for 5 minutes and left to stand for 30 minutes. 4 mL of the upper layer, the middle layer and the bottom layer of the suspension were collected and prepared to a 12 mL solution of respectively to determine the contents of donepezil semi pamoate. The relative concentration differences (RCD) between layers of donepezil semi pamoate were calculated to evaluate the suspension property of different formulations. The results are shown in Table 2.

TABLE 2

| Formulation No. | CMC-Na concentration | Poloxamer 188 concentration | Tween 80 concentration | RCD (%) between layers |
| --- | --- | --- | --- | --- |
| Formulation 01 | 0.75% | 0.2% | / | 1.5 |
| Formulation 02 | 1.0% | 0.2% | / | 0.5 |
| Formulation 03 | 1.5% | 0.2% | / | 0.5 |
| Formulation 04 | 1.0% | 0.05% | / | 1.1 |
| Formulation 05 | 1.0% | / | 0.2% | 1.0 |
| Formulation 06 | 1.0% | / | 0.05% | 1.7 |

As shown in Table 2, the relative standard deviations between layers were all less than 2% for the content of donepezil semi pamoate with different concentrations of CMC-Na (0.75%-1.5%) and poloxamer 188 or Tween 80 (0.05%-0.20%). These results indicate that the above formulations have good suspension effect on donepezil semi pamoate powder.

2. Injectability Study

The diluents containing different concentrations of CMC-Na, poloxamer 188 or Tween 80 were prepared, added with powder 2 # or powder 3 # that prepared in Example 1 to achieve a concentration of powder 2 # or powder 3 # of 230 mg/mL, and then vibrated for a few minutes until forming a uniform suspension. The injectability study was performed by injecting the suspension using syringes with needles at different sizes. Manual injectability is divided into 3 levels: +, ++, and +++, which represent simple for injection, moderately difficult for injection, and quite difficult for injection, respectively. The results are shown in Table 3.

TABLE 3

| Formulation No. | Powder No. | CMC-Na concentration | Poloxamer 188 concentration | Tween 80 concentration | Needle type | | | |
|---|---|---|---|---|---|---|---|---|
| | | | | | 22G | 21G | 20G | 18G |
| Formulation 011 | Powder 3# | 0.75% | 0.2% | / | +++ | ++ | ++ | + |
| Formulation 021 | Powder 3# | 1.0% | 0.2% | / | +++ | ++ | ++ | + |
| Formulation 031 | Powder 3# | 1.5% | 0.2% | / | +++ | +++ | +++ | ++ |
| Formulation 041 | Powder 3# | 1.0% | 0.05% | / | +++ | ++ | ++ | + |
| Formulation 051 | Powder 3# | 1.0% | / | 0.2% | +++ | ++ | ++ | ++ |
| Formulation 061 | Powder 3# | 1.0% | / | 0.05% | +++ | ++ | ++ | + |
| Formulation 071 | Powder 2# | 1.0% | / | 0.05% | +++ | ++ | ++ | + |
| Formulation 081 | Powder 2# | 1.0% | / | 0.1% | +++ | ++ | ++ | + |

Manual test results (Table 3) show that it is quite difficult to inject any one of the suspensions through a 22 G needle. When CMC-Na reaches the highest concentration (1.5%), only an 18 G needle can be used for injection with a moderately difficult level. When the formulation sample has a CMC-Na content of ≤1.0% and a Tween 80 concentration of <2.0%, it can be injected through an 18 G needle.

According to the above comprehensive results of the suspension test and the injectability study, the optimized dose of CMC-Na ranges from 0.75% to 1.0%.

3. Osmotic Pressure Study

Different amounts of mannitol were added into the above diluents in which the concentrations of CMC-Na and poloxamer 188 were fixed as 1% and 0.05%, respectively, and powder 3 # was added to formulate a suspension with a concentration of 230 mg/mL. The osmotic pressure of the suspension was measured.

The results (Table 4) showed that when the content of mannitol was 4.5% to 5.80%, the osmotic pressure ranges from 285 mOsmol/kg to 330 mOsmol/kg.

TABLE 4

Osmotic pressure of diluents containing different amounts of mannitol

| Formulation No. | Mannitol concentration | Osmotic pressure (mOsmol/Kg) |
|---|---|---|
| Formulation 0111 | 4.5% | 285 |
| Formulation 0211 | 4.8% | 292 |

TABLE 4-continued

Osmotic pressure of diluents containing different amounts of mannitol

| Formulation No. | Mannitol concentration | Osmotic pressure (mOsmol/Kg) |
|---|---|---|
| Formulation 0311 | 5.0% | 310 |
| Formulation 0411 | 5.2% | 318 |
| Formulation 0511 | 5.4% | 323 |
| Formulation 0611 | 5.6% | 326 |
| Formulation 0711 | 5.8% | 330 |

Example 4: Preparation of Donepezil Semi Pamoate Injection 7 injection samples of different formulation were prepared according to the amount of each excipient in the formulation of Table 5. The specific preparation steps were as follows: 80% of water for injection and the tension agent were mixed and stirred at 50-60° C. After complete dissolution, CMC-Na was slowly added, stirred, and added with the wetting agent followed by water for injection, to finally formulate to 3 ml dilution solution. The dilution solution was filtered through a 0.22 μm filter membrane, and aseptically dispensed into a borosilicate vial with pyrogens removed. 416 mg of powder injection prepared in Example 1 was dissolved in dilution solution to prepare a donepezil semi pamoate injection when used.

TABLE 5

| Components | Samples Amounts | | | | | | |
|---|---|---|---|---|---|---|---|
| | Sample 1 | Sample 2 | Sample 3 | Sample 4 | Sample 5 | Sample 6 | Sample 7 |
| Active ingredients | Powder 1# | Powder 2# | Powder 3# | Powder 3# | Powder 3# | Powder 4# | Powder 4# |
| Suspending agent | 30 mg CMC-Na | 30 mg CMC-Na | 22.5 mg CMC-Na | 30 mg CMC-Na | 45 mg CMC-Na | 45 mg CMC-Na | 22.5 mg CMC-Na |
| Tension agent | 144 mg mannitol | 144 mg mannitol | 174 mg mannitol | 135 mg mannitol | 23 mg NaCl | 144 mg mannitol | 15 mg NaCl |
| Wetting agent | 1.5 mg poloxamer 188 | 1.5 mg poloxamer 188 | 6 mg Tween 80 | 1.5 mg poloxamer 188 | 3 mg poloxamer 188 | 1.5 mg Tween 80 | 1.5 mg Tween 80 |

TABLE 5-continued

| Components | Sample 1 | Sample 2 | Sample 3 | Sample 4 | Sample 5 | Sample 6 | Sample 7 |
|---|---|---|---|---|---|---|---|
| Water for injection | Up to 3 ml | Up to 3 ml | Up to 3 ml | Up to 3 ml | Up to 3 ml | Up to 3 ml | Up to 3 ml |

The appearance characteristics, particle size, sedimentation volume ratio, redispersibility, syringeability and other items for the above injections were tested according to the "Pharmacopoeia of the People's Republic of China", 2015 edition. The results show that the indices such as appearance characteristics, redispersibility, syringeability and so on all meet the requirements; the sedimentation volume ratio is close to 1; and the particle size of the powder injection is uniformly distributed.

Example 5: Test for Stimulation of Donepezil Semi Pamoate Injection on Rabbit Muscle Local reaction of the injection site was observed after a single injection of donepezil semi pamoate injection to rabbit muscle to preliminarily evaluate the safety of the formulation.

Methods: 12 New Zealand rabbits of clean grade were randomized into 6 groups according to gender and body weight, and 2 animals for each group was used for evaluation. Group 1 was a group of vehicle control in which the dilution solution of excipients of sample 1 in Example 4 without medicament powder was administered. Groups 2-6 were test groups. Among them, powder 1 # in Example 1 was administered to the animals in group 2; powder 2 # in Example 1 was administered to the animals in group 3; powder 3 # in Example 1 was administered to the animals in group 4; powder 4 # in Example 1 was administered to the animals in group 5; and powder 5 # in Example 1 was administered to the animals in group 6. During administration, the medicament powders of groups 2-6 were dispersed into the dilution solution of excipients as used for group 1 with the medicament dose being adjusted to 85.1 mg (based on donepezil) per animal. Each group of animals was administered by a single injection via left quadriceps at a volume of 1 mL per animal.

During the test, the injection site and surrounding tissues were visually observed for red and swelling, congestion, and other stimulations. The observation was performed once a day at the corresponding time after injection.

14 days after the single injection, all test animals were euthanized, and then the left quadriceps of the rabbits were longitudinally incised. The injection site marked during injection was used as baseline, and the adjacent muscles were observed and scored according to the criteria listed in Table 6 below. Finally, comprehensive judgment was made based on the results of visual observation and histopathological examination.

Observation of Injection Site:

The results of visual observation showed that slight hyperemia was observed on day 2 after injection, and erythema was observed on day 2 to day 4 after injection at the injection site for one animal in the group of vehicle control, while the other animal had no obvious symptom at the injection site.

Red and swelling was observed at the injection site for 2 animals in the test group 2 on day 2 to day 4 after injection.

Slight red and swelling was observed at the injection site for one animal in the test group 4 on day 2 to day 4 after injection, while the animals in other groups had no obvious symptom at the injection site on day 2 to day 4 after injection.

On day 14 after the single injection, the tested animals in the vehicle control group and the test groups 3 and 5 showed no histopathological abnormalities; one of the two animals tested in the test groups 4 and 6 only showed slight monocyte infiltration on both sides of skeletal muscle at the injection site, while the other animal had no obvious symptom at the injection site; and the tested animals in the test group 2 showed moderate monocyte infiltration and slight subcutaneous hemorrhage at the injection site of the muscle, and slight hemorrhage and moderate edema in skeletal muscle.

Muscle Stimulation Evaluation:

The scoring of muscle stimulation response is shown in Table 6. The examination results of this experiment are shown in Table 7. It can be seen from Table 7 that the medicament of the test group 2 can cause moderate congestion and edema at the injection site (score=2), while the medicaments of the test groups 3-6 cause a slight hyperemia at the injection site (score=1).

The above observation results show that the injection of powder 1 # prepared in Example 1 has greater stimulation to the muscle at the injection site, while powder 2 #, powder 3 #, powder 4 # and powder 5 # prepared in Example 1 has less stimulation to the muscle after injection.

TABLE 6

| Stimulation response | Score |
|---|---|
| No serious response | 0 |
| Slight congestion, less than 0.5 cm × 1.0 cm | 1 |
| Moderate congestion, greater than 0.5 cm × 1.0 cm, and moderate edema | 2 |
| Severe congestion with muscle degeneration | 3 |
| Necrosis with brown degeneration | 4 |
| Massive necrosis | 5 |

TABLE 7

| Group No. | Group type | Animal No. | Gender | Score on day 14 after injection |
|---|---|---|---|---|
| 1 | Vehicle control | 101 | M | 0 |
|   |   | 102 | F | 0 |
| 2 | Powder 1# | 201 | M | 2 |
|   |   | 202 | F | 2 |
| 3 | Powder 2# | 301 | M | 1 |
|   |   | 302 | F | 0 |
| 4 | Powder 3# | 401 | M | 0 |
|   |   | 402 | F | 1 |
| 5 | Powder 4# | 501 | M | 1 |
|   |   | 502 | F | 1 |

TABLE 7-continued

| Group No. | Group type | Animal No. | Gender | Score on day 14 after injection |
|---|---|---|---|---|
| 6 | Powder 5# | 601 | M | 0 |
|  |  | 602 | F | 1 |

CONCLUSIONS

It can be seen from the experiment that powder 1# prepared in Example 1 can cause a local stimulation response in the muscle at the injection site, while powder 2#, powder 3# powder 4# and powder 5 # prepared in Example 1 only cause slight stimulation response in the muscle at the injection site. It follows that powder 2 #-5 # have relatively higher medicament safety than powder 1 #.

It is well known that for long-acting injection suspensions, when the dosage and the excipients are fixed, the larger the particle size of medicament powder is, the greater the stimulation to the injection site after injection is. However, the present inventors have unexpectedly discovered that the medicament stimulation of medicament powder 2 #, powder 3 # and 4 # having large particle sizes is not larger than that of powder 5 # having a smaller particle size.

The above are only the preferred examples of the present disclosure, and are not intended to limit the present disclosure. Any modifications, equivalents, improvements, and the like made within the spirit and principles of the present disclosure should be included within the scope of the present disclosure.

The invention claimed is:

1. A powder injection of donepezil semi pamoate comprising donepezil semi pamoate crystals, wherein the donepezil semi pamoate crystals have an average particle size of 2-52 μm, wherein the donepezil semi pamoate crystals have an angle of repose of 25-46 degrees, and wherein an injection prepared from the powder injection has less stimulation to the muscle after injection.

2. A method for preparing the powder injection of donepezil semi pamoate of claim 1, comprising:
   step 1: dissolving donepezil hydrochloride in purified water, stirring, and filtering to obtain a filtrate;
   step 2: dissolving disodium pamoate in purified water, stirring, and filtering to obtain a filtrate; and
   step 3: adding donepezil semi pamoate seed crystals to the filtrate obtained in step 1 to obtain a solution, then dropwise adding the filtrate obtained in step 2 to the solution, stirring for 1-2 hours to crystallize donepezil semi pamoate, filtering to obtain a filter cake, washing the filter cake with purified water, drying, and performing a dry pulverization and a sterilization process;
   wherein the sterilization process is a γ-ray irradiation sterilization, an electron beam irradiation sterilization or a microwave irradiation sterilization, and an irradiation dose of the irradiation sterilization is 25 kGy to 60 kGy.

* * * * *